(12) United States Patent
Baruch et al.

(10) Patent No.: US 10,342,437 B2
(45) Date of Patent: Jul. 9, 2019

(54) DETECTION OF PROGRESSIVE CENTRAL HYPOVOLEMIA

(71) Applicants: Martin Baruch, Charlottesville, VA (US); David Gerdt, Faber, VA (US); Charles Adkins, Earlysville, VA (US)

(72) Inventors: Martin Baruch, Charlottesville, VA (US); David Gerdt, Faber, VA (US); Charles Adkins, Earlysville, VA (US)

(73) Assignee: Empirical Technologies Corporation, Charlottesville, VA (US)

(*) Notice: Subject to any disclaimer, the term of this patent is extended or adjusted under 35 U.S.C. 154(b) by 1043 days.

(21) Appl. No.: 14/092,745

(22) Filed: Nov. 27, 2013

(65) Prior Publication Data

US 2015/0148694 A1 May 28, 2015

(51) Int. Cl.
| | |
|---|---|
| A61B 5/02 | (2006.01) |
| A61B 5/021 | (2006.01) |
| A61B 5/00 | (2006.01) |
| G16H 50/30 | (2018.01) |

(52) U.S. Cl.
CPC ...... *A61B 5/02042* (2013.01); *A61B 5/02125* (2013.01); *A61B 5/7275* (2013.01); *G16H 50/30* (2018.01)

(58) Field of Classification Search
CPC .... A61B 5/02125; A61B 5/021; A61B 5/0285
See application file for complete search history.

(56) References Cited

U.S. PATENT DOCUMENTS

| | | |
|---|---|---|
| 4,635,635 A | 1/1987 | Robinette-Lehman |
| 4,726,382 A | 2/1988 | Boehmer et al. |

(Continued)

FOREIGN PATENT DOCUMENTS

| | | |
|---|---|---|
| EP | 90401136.8 | 10/1990 |
| EP | 0926 980 B1 | 10/2008 |
| JP | 155826 A | 6/1999 |

OTHER PUBLICATIONS

Trachet B et al, Numerical Validation of a New Method to Assess Aortic Pulse Wave Velocity from a Single Recording of a Brachial Artery Waveform with an Occluding Cuff, Annals of Biomedical Engineering, Kluwer Academic Publishers.Plenum Publishers, NE, vol. 38, No. 3, Feb. 2, 2010, pp. 876-888.

(Continued)

*Primary Examiner* — Etsub D Berhanu
*Assistant Examiner* — Michael A Catina
(74) *Attorney, Agent, or Firm* — Kimberly O Snead

(57) ABSTRACT

A system for detecting dehydration, hemorrhaging, and increases in blood volume comprising monitors the time difference between the arrival of the primary left ventricular ejection pulse (pulse T1) and the arrival of the iliac reflection (pulse T3) to determine an arterial pulse parameter which is the time difference between T1 T3. Changes in T3 minus T1 are indicative of something happening to blood volume. If the T1-3 value goes up and the patient is on an infusion system, it can be an indication of having too much fluid pumped and if T1-3 is lower than it should be for an individual, they are either dehydrated (which can result in decreases in blood volume), they are hemorrhaging, or they have hemorrhaged. A downtrend in T13 can tell whether someone is continuing to hemorrhage.

14 Claims, 7 Drawing Sheets

(56) References Cited

U.S. PATENT DOCUMENTS

| | | | |
|---|---|---|---|
| 5,709,212 | A | 1/1998 | Sugo |
| 6,319,205 | B1 | 11/2001 | Goor et al. |
| 6,676,608 | B1 | 1/2004 | Keren |
| 2002/0058876 | A1 | 5/2002 | Chen et al. |
| 2007/0016085 | A1 | 1/2007 | Inukai |
| 2007/0225609 | A1 | 9/2007 | Rosch et al. |
| 2009/0326386 | A1 | 12/2009 | Sethi |
| 2010/0262022 | A1* | 10/2010 | Baruch ............... A61B 5/021 600/500 |

OTHER PUBLICATIONS

H Olsen et al "Cardiovascular response to acute hypovolemia in relation to age. Implications for orthostatis and hemorrahge" American journal of physiology, Heart and circulatory physiology, Jan. 1, 2000, pp. H222-232.

William F. Garnett et al, Exercise and Sport Science, Lippincott Williams & Wilkins 1999; p. 146.

Biopac Systems, Inc., website, Noninvasive Blood Pressure System for MRI-NIBP-MRI, Apr. 30, 2010 (http://www.biopac.com/MRI-Compatible-Noninvasive-Blood-Pressure).

Michael Pinsky, Probing the Limits of Arterial Pulse Contour Analysis to Predict Preload Responsiveness, Anesth Analg 2003; 96:1245-7.

Victor A. Converino, PhD, et al; Arterial Pulse Pressure and its Association with Reduced Stroke Volume During Progressive Central Hypovolemia; Journal of Trauma Injury, Infection and Critical Care; vol. 61, No. 3.

Baruch et al; Westwood, JD; Medicine Meets Virtual Reality 15, in Silico: Designing the Next in Medicine; 2007, IOS Press: pp. 40-41.

Robert J. Bache, et al; Left Ventricular Ejection Timein Valvular Aortic Stenosis; Circulationi 1973; 47:527-533.

\* cited by examiner

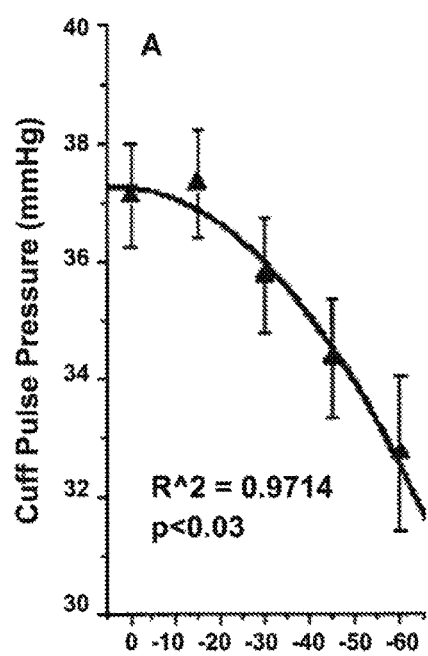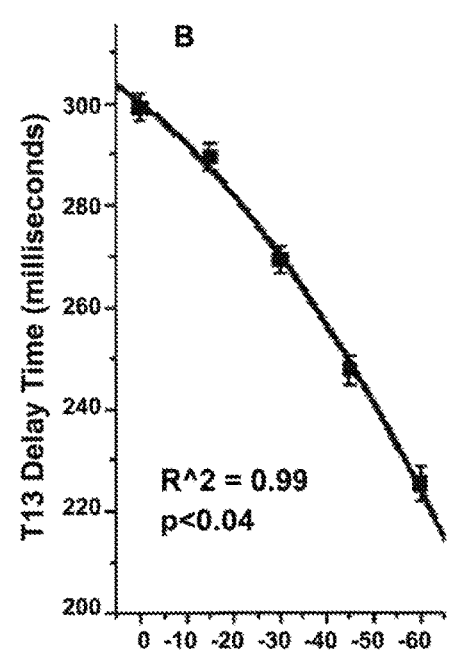
Figure 8 A     LBNP (mmHg)     Figure 8B

United States Patent No. US 10,342,437 B2

DETECTION OF PROGRESSIVE CENTRAL HYPOVOLEMIA

GOVERNMENT INTEREST STATEMENT

ONR (Office of Naval Research) NO-0014-04C-0204

CROSS-REFERENCE TO RELATED APPLICATION

This application is a continuation-in-part of co-pending U.S. patent application Ser. No. 13/231,703 filed Sep. 13, 2011 for Hydrostatic Finger Cuff Blood Wave Form Analysis; Ser. No. 12/854,954 for Hydrostatic Finger Cuff Blood Wave Form Analysis filed Aug. 12, 2010; Blood Pressure Determination Based on Delay Times between Points on a Heartbeat Pulse, pending patent application, Ser. No. 12/537,228 filed Aug. 6, 2009; Method for Arterial Pulse Decomposition Analysis for vital Signs Determination, pending patent: Ser. No. 11/500,558 filed Aug. 8, 2006, which is a C-I-P of U.S. Pat. No. 7,087,025 for Blood Pressure Determination Based on Delay Times Between Points on a Heartbeat Pulse issued Aug. 8, 2006, and Wrist Plethysmograph, Ser. No. 11/803,643 filed May 15, 2007, and Apparatus and Method for Measuring Pulse Transit Time, U.S. Pat. No. 6,723,054 issued Feb. 26, 2001, which is a divisional of Ser. No. 09/763,657, all of which are incorporated herein by reference, as though recited in full.

FIELD OF THE INVENTION

The present invention relates generally to a system for detection of an abnormal decrease in blood volume, and more particularly to detection of a decrease in the volume of blood plasma,

BACKGROUND OF THE INVENTION

There have been many attempts to deduce arterial blood pressure from the time-dependent analysis of the arterial pulse, as opposed to an amplitude-dependent analysis, which cuffs and Tonometers, etc. use. The primary advantages of a time-based blood pressure monitoring system over one based on amplitude analysis are wearer comfort and inherent calibration.

Amplitude-dependent devices have to couple to the pressure wave within the artery and they have to closely track the coupling force with which they bear down on the artery. The required partial occlusion of the artery frequently leads to distinct skin markings as well as numbness of the hand when the radial artery is monitored, which is the most commonly used site for non-invasive blood pressure monitors. In addition, if the device loses track of the force with which it bears down on the artery, either because of drastic blood pressure changes or because of signal-disrupting movements, it has to be re-calibrated. If this requires inflation of a cuff, such as is the case with the Colin Pilot unit, the wearer will experience additional discomfort.

Previous attempts to deduce blood pressure from arterial pulse time domain analysis have used the well-known fact that the propagation velocity of the arterial pulse is highly dependent on the arterial pressure. These approaches have used delay times between arterial pulses measured at different arterial sites, such as the brachial and the radial artery pulse sites, or, most commonly, have used the time delay between the QRS complex of an ECG signal and a pulse measured at an arterial pulse site. In general, such two-site approaches have only been able to track substantial changes in BP using pulse transit time (PTT) but have failed to reliably resolve small changes in BP. An example of a small change in BP that is physiologically important is Pulsus Paradoxus (PP), which is defined as the abnormally large decline in systemic arterial pressure and pulse pressure associated with inspiration, usually due to an airway obstruction such as during an asthma attack.

A further and significant complication in previous PPT measurement approaches has been the determination of the diastolic and systolic BP components. The pulse location in time has usually been determined by establishing a threshold condition near the foot of the arterial pulse, either using a simple percentage of total pulse height rule or other more sophisticated methods, such as the tangent intersection method, which is the intersection of the straight-lines drawn through the rear and the fore-fronts of the arterial pulse wave. Not surprisingly, given the fact that the threshold point is close to the diastolic pressure amplitude range, delay times obtained in this manner have correlated reasonably well with diastolic blood pressure changes. However, two-site measurement approaches have been especially deficient in the measurement of systolic blood pressure variations. This is not surprising because the heartbeat pressure pulse changes dramatically in shape and amplitude as it heads toward the arterial periphery. As a result attempts to compare the time delay evolution of certain points on the pulse measured at different arterial pulse sites, aside from foot-to foot measurements, have been difficult. The changes in pulse shape are due to a number of factors, including changes in the arterial wall material composition that affect the-wall's elastic behavior, the taper of the main arterial branch, the distribution of branch lines, and pulse reflections. The result is that the pulse steepens and contracts as it propagates.

Background of the invention can be found in the following publications, the disclosures of which are incorporated herein by reference:

1—Cooke, William H, and Convertino, Victor A, Heart Rate Variability and
Spontaneous Baroreflex Sequences: Implications for Autonomic Monitoring DuringHemorrhage, J. Trauma, Injury, Infection, and Critical Care, 5~(4):798-805, April 2005.
2—Convertino, Victor A, Cooke, William H. Holcomb, John H, Arterial pulse pressure and its association with reduced stroke volume during progressive central hypovolemia, J. Trauma. 2006; 61:629-634.
3—Davies J I, Band M M, Pringle S, Ogston S, Struthers A D, Peripheral blood pressure measurement is as good as applanation tonometry at predicting ascending aortic blood pressure, J. of Hypertension. 21 (3):571-576, March 2003
4—Leonetti P, Audat F, Girard A, Laude 0, Lefrere F, Elghozi J L. Stroke volume monitored by modeling flow from finger arterial pressure waves mirrors blood volume withdrawn by phlebotomy. Clin *Auton Res.* 2004; 14:176-181.
5—MacDonald's, *Blood Flow in Arteries,* $4^{th}$ ed. Arnold, p. 84, 1998.
6—Anliker M et. al, Transmission characteristics of axial waves in blood vessels, J.
Biomech., 1, p 235-46, 1968

SUMMARY OF THE INVENTION

It should be recognized that reflected pulses readily propagate through the arterial system, and the pulse measured at a certain arterial site is actually a superposition of a number of different and distinct pulse components. Therefore, knowledge of these pulse components and how they travel through the arterial system as a function of blood pressure is essential to make meaningful pulse time delay measurements for the purpose of blood pressure determinations. In the absence of a comprehensive physical understanding of the structure of the pulse in the arterial periphery it is therefore not surprising that commercially viable time-domain analysis approaches of the arterial pulse have so far limited themselves to the determination of arterial pulse propagation velocities alone.

The present invention avoids the problems and disadvantages of multiple site blood pressure measurements provides single-site measurement of blood pressure with less complexity and lower cost than has heretofore been possible. It has now been discovered that a well known pressure-velocity relationship that has been shown to hold for pressure-change induced pulse propagation changes also holds for the components of a single arterial pulse. In addition it has been determined that the component pulses of which the arterial pressure pulse is comprised, can be distinctly determined. Knowledge of where these component pulses originate, what arterial distances they have traversed, as well as their measured relative time delays makes it possible to determine the blood pressures, both systolic as well as diastolic, that influenced their relative delay times.

In contrast with the foregoing systems, a time-based arterial pulse analysis approach is less dependent on the coupling pressure to the arterial pulse. As long as the sensor is linear as well as sensitive enough to record the entire arterial pulse shape with high fidelity, it is possible to deduce from the time evolution of the arterial pulse the blood pressure to which the pulse is subjected. Since such a device does not have to couple to the artery's pressure wave as aggressively, wearer comfort is increased. In addition, by using algorithms that are based on a physiological model of the arterial pulse, the approach is neither subject to continued re-calibrations after motion has occurred, nor otherwise induced disruptions of the signal. This is due to the fact that a time-based arterial pulse analysis approach constitutes tracking the time evolution of physiologically relevant markers in the arterial pulse. As long as the algorithm re-acquires the time positions of the relevant markers, the original calibration that linked diastolic and systolic as well as mean blood pressure components to the time markers will hold. The goal has been somewhat elusive up until now because of the uncertainty of determining physiologically relevant arterial pulse markers.

In accordance with a first broad aspect of the present invention blood pressure (BP), and more particularly non-occlusive, passive blood pressure is measured using a sensor reading of heartbeat pulses at a single site and with a resolution sufficient to resolve small variations in blood pressure. The invention utilizes a primarily time-dependent pulse wave analysis that is based on a physiological model of the components of the arterial pulse. In accordance with a further aspect of the present invention, the problems due to different pressure-induced pulse-shape modulations associated with different pulse detection sites are avoided by detection of single heartbeat pulses at a single site and by analysis of individual pulses. In accordance with another aspect of the invention use is made of the fact that changes in time delay between certain different parts of a heartbeat pulse, subjected to different arterial pressures reflect changes in blood volume.

In accordance with an embodiment of the invention a system is provided for detecting dehydration, hemorrhaging, and increases in blood volume which comprises monitoring the time difference between the arrival of the primary left ventricular ejection pulse (pulse T1) and the arrival of the iliac reflection (pulse T3) to determine an arterial pulse parameter which is the time difference between T1-T3.

Changes in T3 minus T1 are indicative of something happening to blood volume. If the T1-3 value goes up and the patient is on an infusion system, it can be an indication of having too much fluid being infused and if T1-3 is lower than it should be for an individual, they are either dehydrated (which can result in decreases in blood volume), they are hemorrhaging, or they have hemorrhaged. A downtrend in T13 can tell whether someone is continuing to hemorrhage. Measurement of the change of the parameter T1-T3 is carried out in real time. T13 values that are low in comparison to the values for a comparable patient group, such as a particular age group, could indicate with a very short reading that the patient has either had a blood loss or was dehydrated.

BRIEF DESCRIPTION OF THE DRAWINGS

FIG. 8A is a graph illustrating overall results for pulse pressure obtained with the automatic cuff;

FIG. 8B is a graph illustrating overall results for pulse pressure obtained with the PDA pulse pressure-equivalent parameter T1-3. Also shown are results of second-order polynomial fits.

DESCRIPTION OF PREFERRED EMBODIMENTS

Definitions

Figure 1:
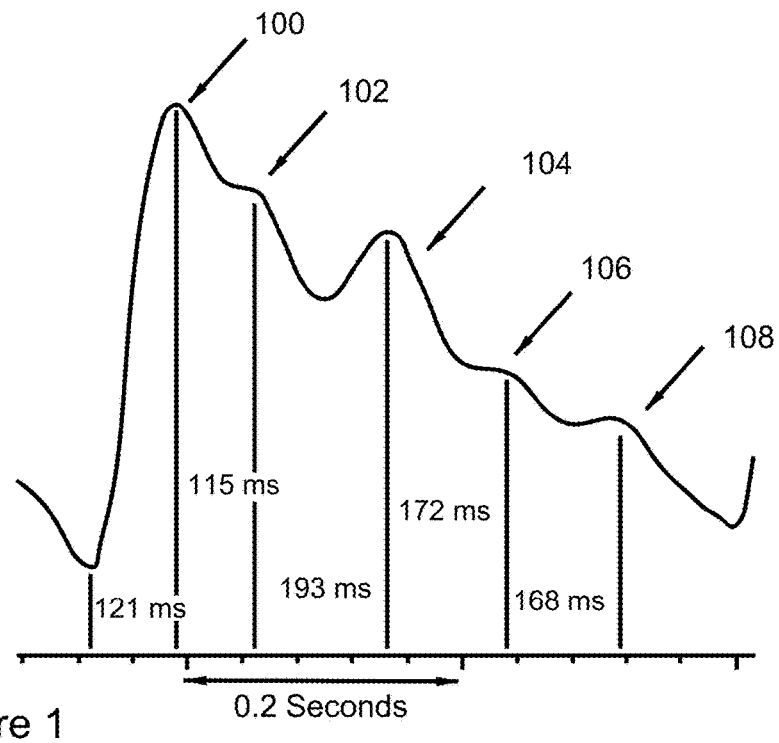
FIG. 1 is a graph illustrating the five constituent pulses that make up the finger pulse.

Where the definition of terms departs from the commonly used meaning of the term, applicant intends to utilize the definitions provided below, unless specifically indicated. For the purposes of the present invention, the term "plethysmograph" refers to an instrument that measures variations in the size of an organ or body part on the basis of the amount of blood passing through or present in the part, For the purposes of the present invention, the term "horse race" refers to a contest of speed among horses that either are ridden by jockeys or pull sulkies and their drivers, For the purposes of the present invention, the term "substantial" refers to an ample or considerable amount, quantity or size. Accordingly, the term "substantially comparable" as employed herein refers to data or information that can enables a diagnosis to be made based on a comparison of the patient's real time data to the substantially comparable data.

For the purposes of the present invention, the term "Valsalva episode" or "Valsalva maneuver" refers to the expiratory effort when the mouth is closed and the nostrils are pinched shut, which forces air into the Eustachian tubes and increases pressure on the inside of the eardrum, and to the expiratory effort against a closed glottis, which increases pressure within the thoracic cavity and thereby impedes venous return of blood to the heart. Essentially, Valsalva maneuver is any attempted exhalation against a closed glottis or against a closed mouth and nose.

A Valsalva maneuver performed against a closed glottis results in a drastic increase in ressure in the thoracic cavity, the airtight section of the torso that houses, the lungs and heart. In normal exhalation, the diaphragm relaxes, pushing up and into the thoracic cavity. This increases pressure in the cavity and forces the air out of the lungs. However, when the air cannot escape, as when the glottis is closed in a Valsalva maneuver, pressure simply continues to build inside the thoracic cavity until the diaphragm relaxes or the air is allowed to escape. This reduces the amount of blood flow into the thoracic cavity, especially in the veins leading to the right atrium of the heart. For the purposes of the present invention, the term "interbeat interval" refers to the time interval between temporally adjacent heartbeat pulses. For the purposes of the present invention, the term "monotonically" refers to the designating of sequences, the successive members of which either consistently increase or decrease but do not oscillate in relative value. Each member of a monotone increasing sequence is greater than or equal to the preceding member; each member of a monotone decreasing sequence is less than or equal to the preceding member.

The system of the present invention uses a pulse decomposition analysis (PDA) and algorithm to determine the changes in both the systolic and diastolic thereby enabling a non-invasive monitoring system for the purposes of predicting the onset of medical conditions. A battery operated fourteen ounce unit tracks systolic, mean and diastolic blood pressure, beat by beat, wirelessly sending the raw data to a PC. Initial values of blood pressure are entered by manual measurement or automatic cuff system. All data is analyzed at the users PC, supplying, plotting and storing results in real time.

Although prior art has used cuffs, the readings obtained have never been able to be used as a determinate of blood pressure changes. The algorithm used in the system of the present invention monitors the time difference between the arrival of the primary left ventricular ejection pulse (pulse #1) and the arrival of the iliac reflection (pulse #3) to determine an arterial pulse parameter T1-T3. T1-T3 may also be referred to herein as T13 or T1 3 and refers to the time differential between T1 and T3. The T13 differential enables system to determine, the onset of conditions such as hemorrhagic shock, blood loss, as well as monitor blood transfusions.

Before describing the details of the invention it is necessary to provide an overview of the physiological model that underlies the approach of the invention. The benefit of the model is that it provides a physiological understanding of the structure of the arterial radial pulse as a result of which arterial pulse analysis algorithms can be developed based on a physical model of the arterial tree, as opposed to for example, implementing a multi-variable mathematical model that correlates newly acquired pulse shapes with a large set of previously stored pulse shapes, or using a generalized transfer function to reverse the filtering effect of the arterial tree on the propagating arterial pulse. While the description given here is limited to applying the model to the radial arterial pulse, it will become clear in the context of the description of the model that it can readily be extended to other pulse sites.

A Model of the Radial Pulse

At the core of the model is the concept that the radial arterial pulse is a superposition of several component pulses. At the temporal front of the radial pulse envelope is the primary pressure pulse that results from the contraction of the left ventricle and the subsequent ejection of blood into the arterial system. Additional component pulses give rise to the temporal features of the radial arterial pulse that follow this primary pulse. Isolation and identification, with regard to time and amplitude, of these individual component pulses provides an analysis from which information about blood pressure as well as arterial tree health can be obtained.

Background

A basic understanding of the physical circumstances of the propagation of the arterial pulse from the heart to the periphery was achieved decades ago. The picture is one of an arterial pressure pulse that originates at the interface of the left ventricle and the aortic root traveling away from the heart through the arterial tree and being reflected at various sites to various degrees. The reflection sites are areas where the arterial tree branches or where different diameter sections join. Both types of sites present an impedance mismatch to the propagating arterial pulse, giving rise to reflections. The existence and the physiological consequences of reflections in the arterial tree are now commonly accepted. One example is the "diastolic wave" which is clearly a reflection phenomenon. In young and elastic arterial trees this reflection arrives back at the heart well into the diastolic phase of the cardiac cycle and has the beneficial effect of raising the blood pressure outside the closed left ventricle, thereby enhancing perfusion of blood into the coronary arteries. As the arterial tree ages and hardens, pulse velocities increase and reflections arrive earlier. Pathologies arise when the reflections arrive while the left ventricle is still open. The heart now has to contract harder to overcome the additional pressure in the aortic root, leading to wall thickening and other complications. Also, since the pressure in the aortic root is now lower during the diastolic phase, perfusion of the coronary arteries is diminished.

The above description of the existence of reflections and their physiological impact is well established in the medical literature. Extensive clinical studies and theoretical modeling efforts have been performed to investigate various aspects of arterial pulse reflections, such as the "second systolic peak", yet no clear model with regard to the radial arterial pulse has been proposed as to where exactly the reflections arise. As an example, an asymmetric T-shaped model where the pulse originates at the T junction and the ends of the T represent generalized reflection sites of the lower body and the upper body, has been proposed. The model does a reasonable job in explaining the shape of the aortic pulse that has been analyzed in detail in a number of clinical studies but it draws no conclusions about what effect these findings should have on the shape of the pulse in the arterial periphery, such as the radial pulse. To begin, why is it reasonable to assume that there are distinct reflection sites in the arterial tree as opposed to the assumption that, as an example, "the lower body" as a whole gives rise to the reflections that have such physiological significance to cardiac health? The answer is two-fold. One is that the features of the reflected wave are too distinct, and too sharp, as to be the convolution of different reflections originating from different sites with different time delays and different reflection coefficients, which would tend to broaden out specific pulse features. The second answer is that the arrival times of the specific features of the radial pulse very much narrow the location possibilities of the reflection sites that gave rise to them.

One feature almost all of the radial pulse signatures share is the fact that they exhibit pulse like protrusions that have a time duration comparable to that of the primary pulse. One consequence of Valsalva is the shortening of the cardiac ejection period as a result of which it is possible, in a comparatively young and elastic arterial tree, to see the complete separation of primary pulse and reflected pulse. Clearly the reflected pulse shows no broadening compared to the primary systolic peak, supporting the hypothesis that it originated at a distinct refection site.

While a distinct reflection site will give rise to a reflection that bears strong resemblance to the primary pulse, distributed and multitudinous reflection sites will give rise to a plethora of reflected pulses, arriving at different time delays and with different amplitudes. The superposition of such a system of reflection sites will be a featureless, broadened pulse. The presence of distinct pulse-like features in most of the radial signatures shown therefore suggests that, past the primary systolic peak, distinct reflection sites are responsible for the sequence of reflected pulses that comprise the "diastolic wave". While the presence of distinct pulse-like features in the radial pulse suggests the existence of distinct reflection sites, their time of arrival relative to the primary pulse makes the argument significantly more concrete.

Since arterial pulse propagation velocities have been measured throughout the body, it is possible to match time delays with potential reflection sites. If one uses approximate arterial distances and their respective velocities, the "second systolic" peak matches readily with the site labeled "reflection site I" while the third peak matches with "reflection site II". In light of results published twenty years ago these conclusions are not surprising.

In 1985 Latham performed a detailed experimental study to map out the shape of the pressure pulse in the different sections of the aorta using a specially designed catheter with spaced micromanometers. His work clearly demonstrated the existence of two major reflection sites to the down-ward traveling arterial pulse, one being in the region of the renal arteries, the other beyond the bifurcation of the iliac arteries. At the location of the renal artery the diameter of the aorta, which tapers continuously away from the heart, undergoes its greatest change. This discontinuity presents a significant impedance mismatch to the traveling pressure pulse, as a result of which an appreciable part of its amplitude is reflected. The reflection can be reduced using the Valsalva maneuver, which involves exhaling into closed airways. As a result of the increasing pressure within the thoracic cavity the diameter of the thoracic aorta decreases (on the order of 17% as Latham verified ultrasonically). The maneuver therefore alleviates the aortic diameter change at the renal arteries, which reduces the impedance mismatch, thereby lowering the site's reflection coefficient.

Latham also found a second reflection site beyond the bifurcation of the iliac arteries, the contribution of which to arterial pulse reflections in the aorta was ascertained using manual femoral artery occlusion maneuvers. Other contributions to the tail end of the aortic pulse were attributed to diffuse arterial pulse reflections from the periphery. In view of Latham's work it therefore seems very likely that the two peaks visible past the systolic peak originate at the reflection sites indicated. Valsalva experiments performed as part of this work further support the model.

The next peak in the radial pulse, that is, the "diastolic peak", as well as the peaks that follow likely arise from the iliac arteries reflection site and not, as Latham had proposed, due to diffuse reflections from the arterial periphery. Latham's explanation with regard to the structure appears to be unlikely, given the distinct peak structure with a spacing comparable to that of the "second systolic" and the "diastolic" peak. Furthermore, the time delay of such reflections would extend up to 250 ms past the "diastolic" peak if some of them truly traversed the length of the legs. Indeed, recent work supports the hypothesis that the peaks visible past the "diastolic" peak are in fact due to re-reflections between the two reflection sites, a reasonable proposition given the strength of the sites' reflection coefficients (10-15% in the case of the renal arteries reflection site, up to 30% in the case of the iliac arteries reflection site).

J. Kriz et. al. showed that it is possible to use force plate measurements as a noninvasive method to perform ballistocardiography, the motion of the body associated with heart activity, by displaying the motion of the heart muscle and the subsequent propagation of the pulse wave along the aorta and its branches, With subjects lying horizontally on a bed that was placed on a force plate they were able to identify the ground reaction forces arising from such center-of-mass altering events as the heart muscle contraction as well as the resulting blood pulse flow. The resolution of the apparatus was sufficient to clearly resolve events involving the redirection of momentum of the propagating arterial pulse, such the pulse's traversal of the aortic arch, its partial reflection at the renal artery site, the iliac reflection site, as well as the subsequent re-reflections of the reflected pulses. As an aside, in subjects with an aortic aneurism, the site of the arterial distension was clearly identifiable due to its effect on the neighboring "normal" reflection sites.

The basic model of the radial arterial pressure pulse is therefore one of a convolution of the primary systolic peak, its single-pass reflections from the renal arteries and iliac arteries reflection sites, as well as their double-pass re-reflections, In order to understand the details of this time delay contraction, one has to be able to determine the arrival times of the individual component pulses at the wrist independently of each other, that is, an "external" clock, as opposed to one started at the onset of a given radial pulse, is required to time the separate arrivals, One means of establishing an "external" clock is to use an ECG signal relative to which the arrival time of each component pulse at the radial artery is measured. Using the Colins Pilot tonometric blood pressure monitor, a subject's ECG and blood pressure was collected in addition to the wrist sensor signal in real time during periods of rest and during the course of a Valsalva maneuver. As one would expect, the oscillations in the delay time of the #1 pulse mirror the pressure oscillations. This is to be expected since pulse travel time and pressure are inversely related. In contrast to the #1 pulse, the delay time of the #2 pulse is far steadier, showing no obviously matching modulations. This is also to be expected because the #2 pulse, after traveling to the renal reflection point at systolic pressure, returned as a reflection at a much lower pressure. It also traversed only the softest part of the aorta, the section above the renal reflection point. Consequently, its velocity will be least affected by arterial pressure changes. In line with this, one would expect the #3 pulse to exhibit a higher sensitivity to changing blood pressure environments. From the Kriz experiments it appears that the iliac reflection is a far more pronounced reflection site than the renal site (as a result of which the #3 peak is also usually significantly larger in amplitude than the #2 peak in the radial arterial pulse spectrum. Consequently, the #3 pulse, which on its primary path to the iliac reflection site, traversed the stiffer and therefore faster abdominal aorta as well as the fast iliac arteries, and returns as a reflection at a higher pressure and therefore higher velocity, compared to the #2 pulse. Traveling at a higher pressure subjects the #3 pulse, similarly but not quite as strongly as the #1 pulse, to the steeper part of the arterial non-linear relationship between pressure and velocity.

Another subtle but very important detail is visible in the evolution of the arrival times of the component pulses during the Valsalva maneuver. The #3 pulse responds first to the rising pressure at the onset of Valsalva. Visual inspection establishes readily that both the arrival time of the #1 pulse as well as the BP line shapes measured with the Colins monitor move off their baseline well after the marker while the arrival time of the #3 pulse has responded well before (approximately 4 seconds before the Colins signals and the #1 component pulse). The delayed reaction of the Colins signals and the #1 component pulse relative to the response of the #3 pulse is a result of the different Young's moduli of the involved arteries, in the absence of significant hardening of the central arteries (the subject in this case is a 46 year old runner in fit shape), the arterial walls in the arm, and in the arterial periphery in general, are significantly tougher than those of the central arteries, a well-known fact due to different elastin versus collagen content in the walls. Since a given rise in blood pressure will tend to distend the softest sections of the arterial tree first, it is entirely reasonable to expect the pulse propagation velocities of the central arteries to also increase first, Consequently one would expect the #3 pulse, which samples the entire aortic tree twice along its propagation path, to accelerate relative to the #1 pulse, which traverses essentially only the arm complex arteries that are characterized by significantly less compliant wall material. The same reasoning explains the time delay between the response of the #3 pulse and the onset of the Colins monitor, which measures its signal at the radial artery.

How the time delay between the #1 and the #3 pulse evolves as the pressure continues to rise is also determined by the differential Young's moduli of the arm and central arteries. In persons with "elastic" central arteries one observes the continued narrowing of the time delay between the #1 and the #3 pulse with rising pressure, indicating that propagation velocities the central arteries, due to their significantly higher distensibility, continue to change faster than those of the arm complex and the arrival time of the #3 pulse changes faster due to the much longer path length over which velocity changes can manifest themselves. In persons with "hard" central arteries, the time delay between #1 and #3 is markedly different. In the case of "hard" central arteries the time delay between #1 and #3 increases with rising blood pressure. Since in this case the central arteries have very little excess distensibility relative to the arm, or peripheral, arteries, the arm arteries respond equally to a rise in pressure. However, due to the higher pulse velocity propagation and the higher gain of the pulse propagation velocity as a function of pressure in the arm versus the central arteries, the #1 pulse continues to accelerate away from the #3. Remarkably, it is possible to observe an intermittent state of the evolution of the delay time between #1 and #3 in the same patient, that is, in the presence of continuously rising pressure, the delay time initially decreases, reverses, and then continues to increase.

Clearly such patients have only some hardening of the central arteries as a result of which they exhibit the pressure onset behavior of patients with "elastic" arteries. The limits of "easy" distensibility are, however, quickly reached and the pressure load is increasingly shared by the peripheral, and specifically the arm, arteries as a result of which, for the same physical reasons that were given above, they exhibit the delay time behavior of "hard" artery patients at higher pressures.

Returning once more to the case of persons with "elastic" central arteries, the reversal of the delay time between #1 and #3 with increasing blood pressure may also occur in this case, but at a much higher pressure. Whether this effect exists, remains to be seen. While the time evolution of T13 (time delay between pulse #3 and pulse #1) as well as the relative amplitude of P3 and P1 is comparatively straightforward, the time delay and amplitude evolution of the pulse relative to the P1 pulse is somewhat more complex. This is due to the fact that the P2 pulse has an additional degree of freedom relative to the P1 and P3 pulses in that its amplitude relative to the other two pulses changes with blood pressure, specifically pulse pressure. This point is perhaps more clearly made after first examining the amplitude evolution of the P3 and P1 peaks as a function blood pressure, specifically systole. The P3 pulse arises from the reflection site in the vicinity of the iliac arteries. This reflection is due to a combination of effects due to arterial bifurcations as well as changes in arterial diameter. Ageing effects, such as through the deposition of plaque, will also alter the reflection site, but these are long-term and slowly-varying effects. In contrast, the physical parameters of this reflection site are not likely to change appreciably with blood pressure. Put differently, the reflection coefficient of the site is not very pressure dependent. Therefore, if the amplitude of P1 increases because the systolic blood pressure has increased relative to the diastolic floor, P3 should increase proportionally, or the ratio of P3/P1 should remain largely constant with changes in blood pressure. Observations to date have shown this to be the case.

In contrast to the amplitude response of P3, which maintains its proportionality to P1, the ratio of amplitudes P2/P1 increases proportionally with blood pressure. This is not surprising since the fact that the "second systolic peak" becomes very prominent in cases of high blood pressure is well known and readily observable. The P2 pulse arises from the reflection site at the height of the renal arteries that is characterized by a diameter mismatch between the thoracic and the abdominal aorta. With increasing blood pressure the thoracic aorta's diameter increases and it does so at a faster rate than the abdominal aorta due to a difference in wall material strength. Consequently, the amplitude of the P2 pulse will increase at a different rate than the P1 with increasing blood pressure, that is, the ratio P2/P1 will increase. The increased amplitude of the P2 pulse will also modify its propagation velocity, which depends highly on the pulse's amplitude. The resulting non-linear delay time behavior, which is due to the fact that the pulse increasingly accelerates as its amplitude rises, can be observed in large-amplitude blood pressure variations such as are observed in dialysis patients.

A final consideration that completes the description of P2's temporal and amplitude evolution is the fact that its amplitude is actually proportional to pulse pressure, that is, the difference between systolic and diastolic pressure. This of course is also the case for P3, since it is only the pulsatile part of the blood pressure that can produce a reflection. In the case of P2, however, the fact that its amplitude changes relative to the amplitude of P1 gives rise to the interesting opportunity that the ratio of P2/P1 is a measure of the pulse pressure, self referenced within each heartbeat pulse and therefore largely independent of coupling efficiencies.

While the systolic pressure is determined using T13, the pulse pressure is tracked by monitoring the ratio of the amplitudes of the #2 and the #1 pulse, i.e. P2/P1, which rises monotonically with pulse pressure. The starting values for correlating P2/P1 with pulse pressure are however very different for different patients since the ratio is small for patients with "hard" central arteries (on the order of 0.04), and larger (0.2) for patients with "elastic" central arteries at comparable normal blood pressures. Patients with hard central arteries tend to have, at normal blood pressures, diminished P2 amplitudes, which increase dramatically with rising blood pressure. Patients with "elastic" central arteries tend to have very pronounced P2 amplitudes at resting blood pressures, indicating that their thoracic aortas are significantly more distended than patients with "hard" central arteries at comparable blood pressures. This observation is supported by published results that demonstrated a drop in aortic pulse propagation velocities by about 10% in subjects who changed from a sedentary lifestyle to one characterized by endurance exercise training. The effect, which was demonstrated to be entirely reversible with cessation of exercise, was shown to be due to a change in aortic distensibility.

With the blood pressure extremes determined, the mean arterial pressure is then determined by obtaining the ratio of the integral over the line shape of the full radial arterial pulse to the time interval over which the integral is performed, a standard procedure. It is clear from the above example and the previous discussion of the influence of the reflection sites on the component pulse amplitudes that, by comparing ratios of the relative amplitudes of the three (or more) component pulses, the relative magnitudes of the renal and iliac reflection site coefficients, or RFL2 and RFL3, can be determined. The reflection coefficient associated with the interface between the arterial junction between the aortic arch and one of the subclavian arteries, RFL 1, has to be determined independently and in the present analysis it has been simply set to 10%. However, its influence on the analysis is minimal since its effect is common to all pulse paths. In addition the RFL 1 coefficient is, similarly to the reflection coefficient RFL3 associated with the iliac reflection site, not likely to change except over significant time frames that allow for relatively slow physiological processes such as, for example, the deposition of atherosclerotic plaque to take place. It is also clear that the effectiveness of implementing the model presented above depends entirely on the efficiency of the algorithms that are used to detect a. the individual radial heart beat pulses and b. the composite pulses that comprise the radial pressure pulse shape. One approach to detect the heartbeat pulses as well as the composite pulses will now be described in detail. It is understood that a plethora of different approaches are available to accomplish the same tasks.

Figure 2:
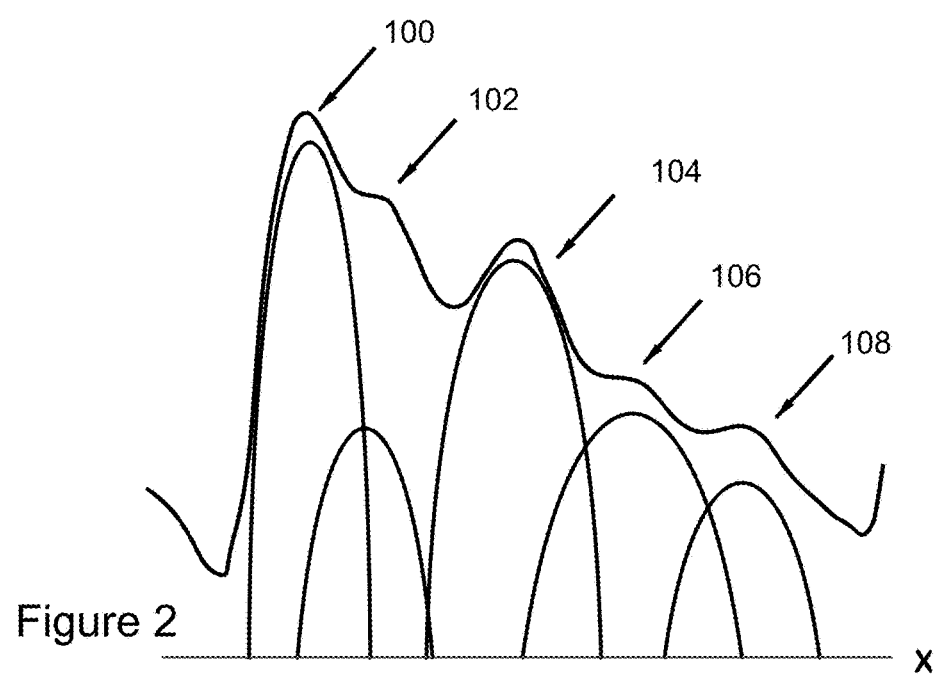
FIG. 2 is a second graph of the five pulses used to constitute a finger pulse.
Figure 3:
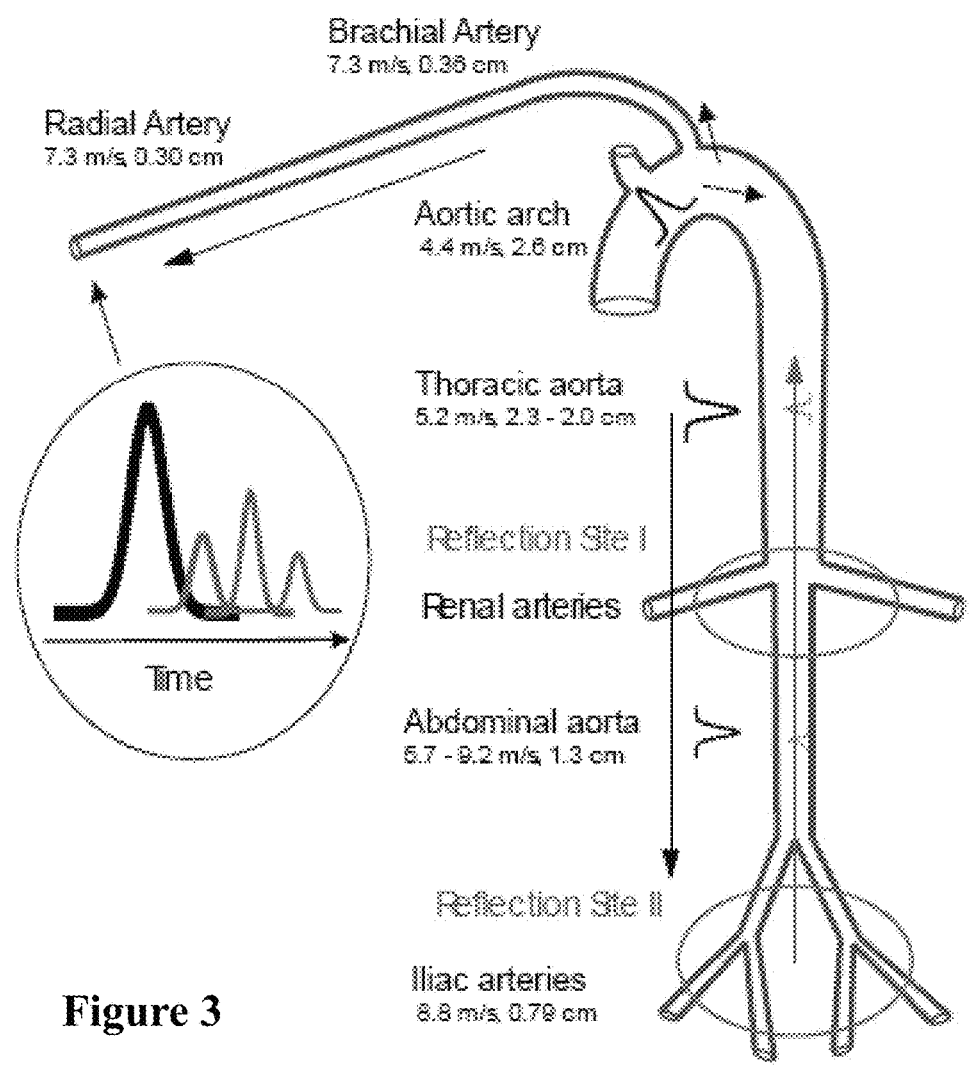
FIG. 3 is a drawing of the arteries involved in creating the pulses of FIGS. 1 and 2.

FIGS. 1 and 2 are graph that illustrate the five constituent pulses that make up the finger pulse in an example pulse waveform taken on a finger using the instant system. In this example, the primary systolic peak T1 100, renal reflection peak T2 102, iliac reflection peak T3 104, re-reflection peak 106 and re-re-reflection peak 108 are illustrated. P2/P1 indicates the relative amplitude of P2 track systolic blood pressure and T1,3 is the time between the two pulses T1 100 and T3 104. It should be noted that pulse creating T1 100 from the left ventricular ejection, travels at a velocity in the systolic pressure regime while the pulse of T3 from the iliac reflection travels at a velocity closer to the diastolic pressure regime. FIG. 3 is a drawing of the arteries that are involved in the pulses of FIGS. 1 and 2.

An algorithm for use in the present invention is disclosed in patent application Ser. No. 11/500,558, filed, Aug. 8, 2006, "Method for Arterial Pulse Decomposition Analysis for Vital Signs Determination", which application is a continuation-in-part of U.S. Pat. No. 7,087,025, entitled, "Blood pressure determination based on delay times between points on a heartbeat pulse", all of which are incorporated herein by reference, as though recited in full.

T1-T3 can also be found from other algorithms or methods, which could include hard wire circuits and no software. The key point is finding the center of the primary peak (in time) and the center of the iliac reflection (third peak, second reflection). Once found, both are simply time in milliseconds. Changes in T3-T1 are indicative of something happening to blood volume.

Automatic infusion pump systems will require blood pressure measurement as near to continuously as possible. The fastest of conventional, automatic arm-cut systems measures systolic blood pressure everyone or two minutes which takes a minimum of 15 seconds per measurement. This load on the arm is not pleasant after a short time. In the fastest conventional systems, the power requirements are high because the pumps are large and powered for high duty cycles. The disclosed system measures blood volume every heartbeat for over 12 hours on a cell phone battery and causes no discomfort. If the T1-T3 value goes up and the patient is on an infusion system, it would be an indication of having too much fluid pumped in (very dangerous especially in the elderly, because it blows out organs), if T1-T3 is lower than it should be for an individual, they are either dehydrated, they are hemorrhaging, or they have hemorrhaged. The trend in T1-T3 can tell whether someone is continuing to hemorrhage.

Although not always necessary, the monitoring of T1-T3 frequently provides the greatest value when performed in real time. "Real time", as used herein, refers to the actual time that it takes a process to occur. In the present system information/data is updated in real time. In the area of computer science, the term "real time" refers to the time it takes for a process under computer control to occur. In computer systems information is updated at the same rate they receive the information, that is, immediately.

In one embodiment of the invention, the system of the present invention operates in real time to measure T1-T3 over a period of time that is sufficient to establish changes or trends in T1-T3 over an extended period of time. The time periods of the testing as well as the intervals between tests can vary depending on the condition being monitored and the protocol of the parties monitoring. In a hospital some protocols will call for measuring beat by beat, for example during major surgery, while others will measure over a predetermined time period. Trends and base lines for a person can be obtained after a few periods, or intervals, however generally the length of the testing period is at least about fifteen (15) seconds.

For example, intermittent testing can be taken, approximately at 15 minute intervals. The time period for the testing can range from a few minutes to a half hour, with 10 to 20 minutes being preferred range for certain applications. The intervals for testing in a battery operated system can also be based on the battery life in addition to patient condition.

The critical factor is to establish a baseline so that deviations can be recognized immediately. Deviations from established baseline will mean more as the base line is known with greater accuracy. Deviations from baseline can from either blood loss or dehydration.

It is likely that T13 does not change appreciably for an individual, except over many years. A baseline could be established either by 15 seconds of continuous measurements or by the equivalent number of heart beats obtained at discontinuous times, say at random time intervals over an hour.

In another embodiment of the invention, the system of the present invention measures T13 for a particular patient and compares the T13 to known values (also referred to as historical data) for a comparable patient group. A comparable patient group, as employed herein, refers to a group having features in common with the patient undergoing monitoring. The features can be equivalent, or at least sufficiently similar to be worthy of comparison and can include age, physical build, similarity of employment, life style, general health, etc. Data of a comparable patient group can be relied upon to prove data sufficiently similar or equivalent to that of the patient to enable a diagnosis to be made in the absence of, or in addition to a patient's personal historical data.

Applications of the System of the Present Invention

With respect to uses of the system of the present invention, in the case of marines or soldiers, T13 is likely similar with all of them and somewhere a little above 300 msec. It is fairly stable with an individual and seems to decrease with age. If someone normally had a T13 of about 300 and one measurement showed it was 250, then either they are dehydrated or they have lost a lot of blood. T13 values that are low for say a particular age group could indicate with a very short reading that this person either had lost blood or was dehydrated. Dehydration also results in decreases in blood volume, It is known that thoroughbred horses have bleeding lungs after a race. The disclosed system has been used to measured pulse patterns in horses and have achieved the same results as with humans using the T13 deviations as an indicator to hemorrhaging.

Dehydration is probably the most important parameter for troops in many countries such as Iraq and Afghanistan however there is no good way to measure it, Dehydration is also a problem in horses, especially work and race horses, and although you can pinch their necks and see how long the pinch marks take to go away; this procedure provides a very approximate test. Using the disclosed system, dehydration can determined by monitoring the deviation from the baseline of either the individual, if known, or a comparable group.

A quick test, using the disclosed system, in the absence of dehydration, can be conducted to see if someone has hemorrhaged. Longer term measurements can be used to monitor the rate of hemorrhaging, Dengue fever can get very serious if and when and hemorrhaging starts (dengue hemorrhagic fever). Most health providers feel the stomach to see if it is hard like wood; however, at that point, it is very late for treatment with coagulants. Dengue fever outbreaks have occurred worldwide and there have been reported cases in Florida and Texas creating a concern about dengue hemorrhagic fever in the United States. The system of the present invention can be used to monitor a patient for hemorrhaging, and is particularly useful in regard to dengue hemorrhagic fever because it is a non-invasive test that can be used to monitor a patient for extended periods of time, as for example, for hours, days, etc.

Experiments/Testing

Tests of the system of the present invention were performed at the Cardiovascular Physiology and Rehabilitation Laboratory of the University of British Columbia on fifteen healthy volunteers (average age: 24.4 years, SD: 3.0 years; average height: 168.6 cm, SD: 8.0 cm; average mass: 64.0 kg. SD: 9.1 kg) whose lower bodies, from the height of the navel down, were subjected to increasingly negative pressures. Lower body negative pressure (LBNP) is an established technique used to physiologically stress the human body, particularly the cardiovascular system. LBNP is used to simulate gravitational stress, to simulate hemorrhage, alter preload, and to manipulate baroreceptors. A number of studies have demonstrated that it is possible to simulate significant internal hemorrhage using LBNRP Negative pressures of 10-20 mmHg correspond to 400 to 550 ml of central blood loss, 20-40 mmHg correspond to 500 to 1000 ml, and negative pressures in excess of −40 mmHg correspond to blood losses exceeding 1000 ml. See publication 1 for background.

The subjects were subjected to four stages of negative pressure, −15 mmHg, −30 mmHg, −45 mmHg, and −60 mmHg, each stage lasting typically about 12 minutes. The blood pressure was monitored with an automatic cuff (Bp TRU Automated Non-lnvasive Blood Pressure Monitor (model BPM-100), VSM MedTech Devices Inc.) set to record blood pressures every three minutes, resulting in typically four readings per LBNP setting, and a pulse oximeter (Ohmeda Biox 3740 Pulse Oximeter, BOC Health Care) monitored oxygen saturation. The System of the present invention collected arterial pulse shapes via a finger cuff attached to the central member of the middle digit. Four subjects became presyncopal and could not complete the −60 mmHg LBNP stage. Both real-time as well as statistical results in the form of regressions are presented. Statistical data are presented as means±standard error.

Results Heart Rate Changes

Figure 4:
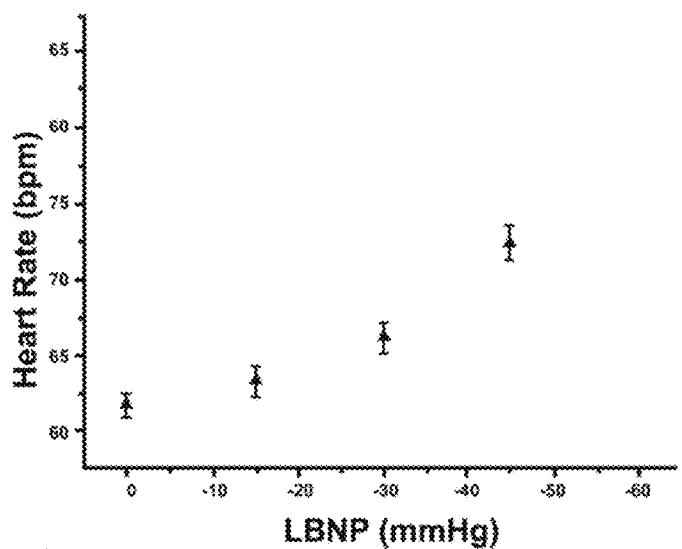
FIG. 4 is a graph illustrating an overall change in heart rate as a function of lower body negative pressure (LBNP) for 15 subjects.
Figure 5:
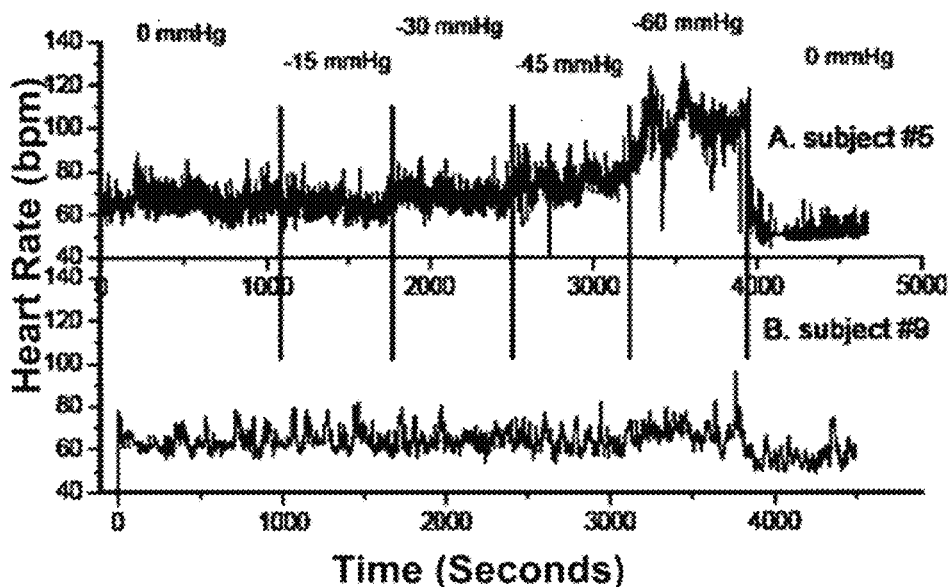
FIG. 5 is a graph illustrating the evolution of heart rates for two subjects of the entire course of their LBNP session showing that while subject #5's heart rate responds strongly, and subject #9's heart rate responds negligibly.

Most of the subjects responded with significant increases in heart rate to the increasing negative pressure. FIG. 4 presents the overall means of heart rates obtained with the system of the present invention for all fifteen subjects. The average effect is clearly resolved, a result that has been verified by other investigators. See for example, publication 2. It is however also well known that heart rate is of limited value as a determinant for the onset of hemorrhage. FIG. 5 presents the heart rate histories of two subjects over the entire course of progressively increasing LBNP and the subsequent venting of the chamber. While in the case of subject #5, as shown in FIG.

5 the heart rate increases significantly. In the case of subject #9 there is next to no discernible change during the progressive LBNP increases, as shown in FIG. 2B.

Cuff-Based Systolic & Diastolic Blood Pressure Changes

Figure 6:
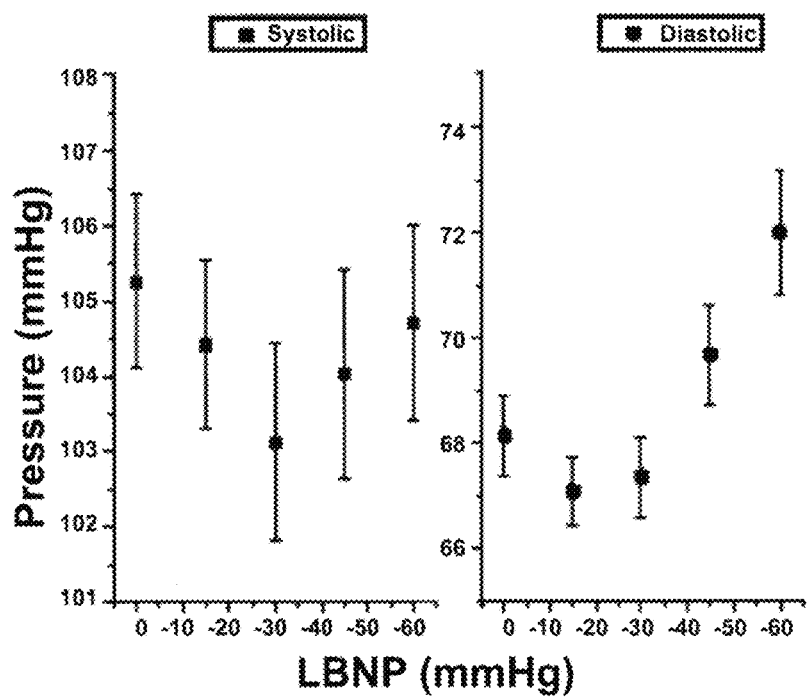
FIG. 6 is a graph illustrating overall study results for systolic and diastolic blood pressures obtained with an automatic cuff.

In regard to the systolic blood pressure recorded with the automatic cuff, next to no correlation with LBNP was determined. The diastolic pressure showed a modest increase with increasing LBNP. These results are presented in FIG. 6. They are in contrast to those reported in publication 2, which reported a decline in systolic pressure of 18 mmHg with increasing LBNP (same range as used here) and next to no change in diastolic pressure in a cohort of subjects with an average age of 15 more years than the subjects studied here.

In contrast to the cuff results the PDA parameter that is equivalent to systolic pressure, the P2:P1 ratio did show a statistically significant decrease with LBNP. This PDA parameter is determined by taking the ratio of the amplitude of the renal reflection pulse (#2 pulse) to the amplitude of the primary left ventricular ejection pulse (#1 pulse).

Figure 7:
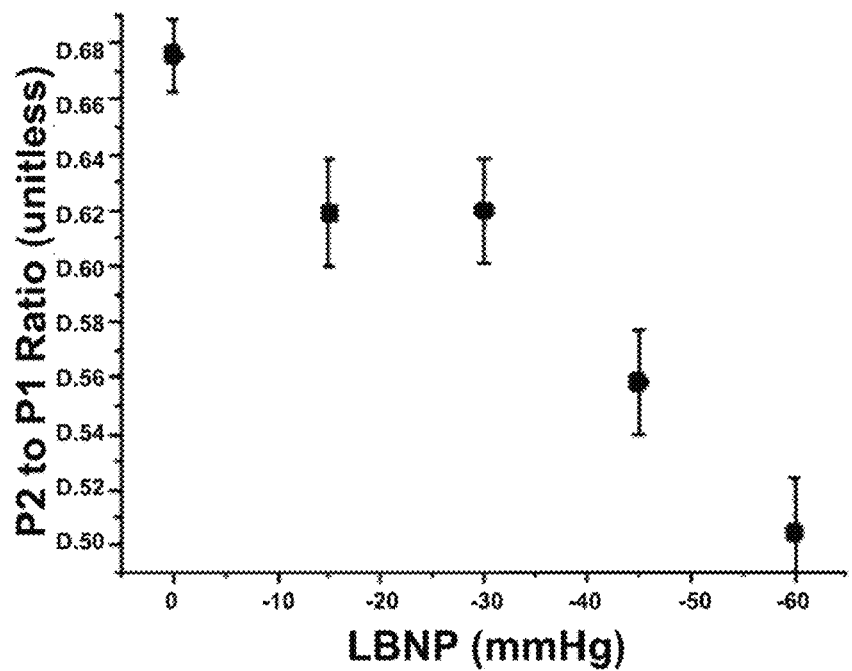
FIG. 7 is a graph illustrating overall results for the P2-P1 ratio, the PDA parameter that is equivalent to' systolic pressure, as a function of LBNP.

These results are presented in FIG. 7. However, while the average effect had statistical significance, no consistent trend was recorded across all subjects, a result verified in other studies that have found that systolic pressure is not a reliable predictor for central blood loss.

In regard to the discrepancy between the automatic cuff results obtained in publication 2 and in this study it is important to note that the blood pressure ranges reported here are very small; on the order of 5 and 8 mmHg in the case of the systolic and diastolic pressures, respectively. It is very difficult to resolve blood pressure trends within such small limits with automatic brachial cuffs due to their instrumental uncertainties and differences in proprietary algorithms. As an example, one study that compared the performance of brachial cuffs and catheters revealed standard deviations (SO) on the order of 12 mmHg with essentially zero bias in the case of systolic blood pressures and 50 s of the order of 12 mmHg as well as a positive bias of 10 mmHg in the case of diastolic pressure measurements. See publication 3 for background information.

Pulse Pressure Changes

Recent work by others (see publications 2 and 4) suggests that pulse pressure is a reliable early predictor of central blood loss since lower central blood volume reduces cardiac filling and therefore stroke volume, which, along with arterial compliance, determines pulse pressure. Since, as studies have shown, both of these physiological parameters decrease during central blood loss, the decrease in pulse pressure is to be expected. This study's results support that hypothesis.

FIG. 8A presents the overall pulse pressure results of the automatic pressure cuff as function of L8NP while FIG. 8B presents the overall results of the pulse pressure equivalent POA arterial pulse parameter T1-3, which is the time difference between the arrival of the primary left ventricular ejection pulse (pulse #1) and the arrival of the iliac reflection (pulse #3). It is seen that while both measurement methods resolve the effect at a statistically significant level, the ability to make a real-time determination of the onset of hemorrhage in individual cases using the two methods differs greatly.

Figure 9:
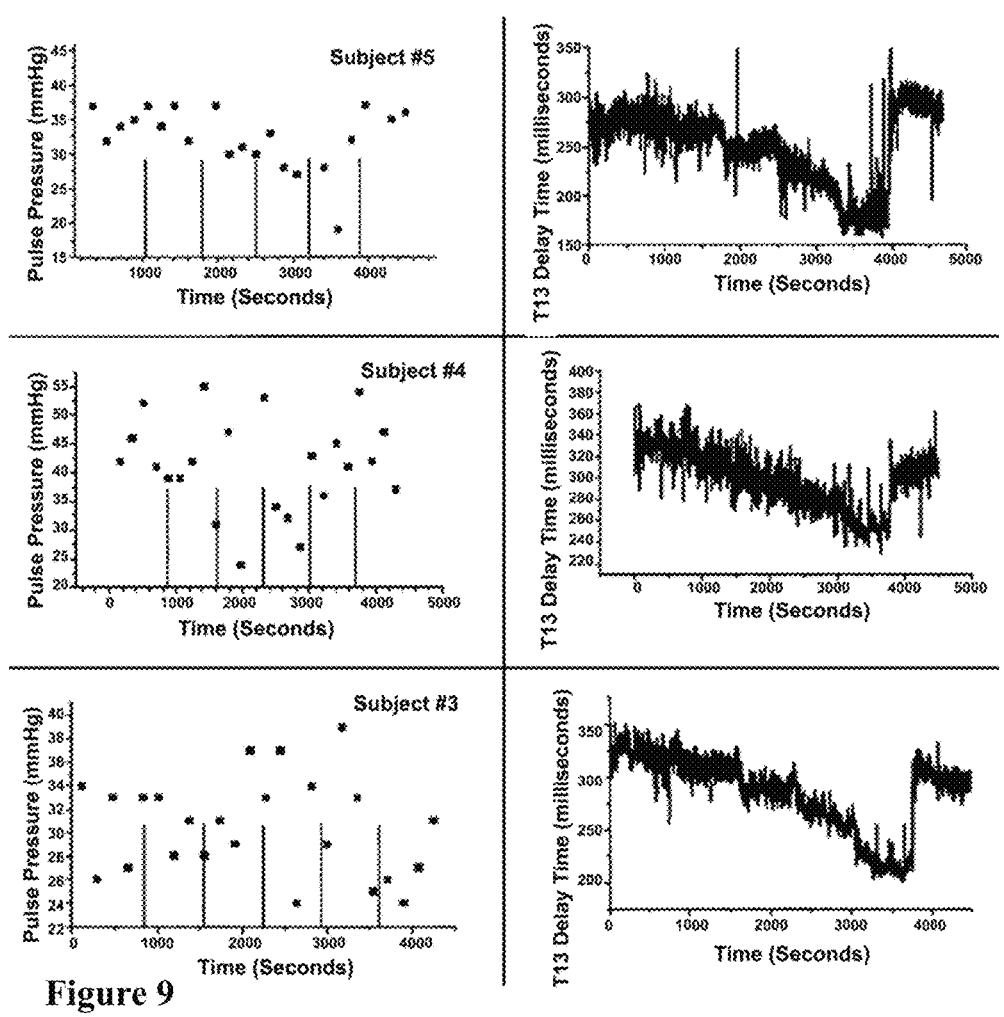
FIG. 9 is a graph illustrating the comparison of the individual results for cuff-based pulse pressure and PDA based T1-3 measurements for subjects 3-5.

FIG. 9 presents side-by-side comparisons of pulse pressures obtained with the automatic cuff (left column graphs) and the histories of the T1-3 parameter over the course of L8NP session, (right column graphs). The right panels present the simultaneously obtained T1·3 delay times between the primary left-ventricular ejection pulse and the iliac reflection pulse recorded on the subjects middle member of the middle digit. The top row presents graphs of the most clearly resolved change in pulse pressures determined with the automatic cuff, left, and of the change in the T1-3 parameter, right, for subject #5. The center row presents the same for subject #9. This is the same subject whose heart rate did not respond to the LBNP changes, which were presented in FIG. 5. Similarly, the cuff-based pulse pressures show no discernible trend. The situation is quite different with regard to the T1-3 parameter whose temporal evolution reveals the plateaus of the individual LBNP stages. The bottom row presents the same comparison of results for subject #3.

Figure 10:
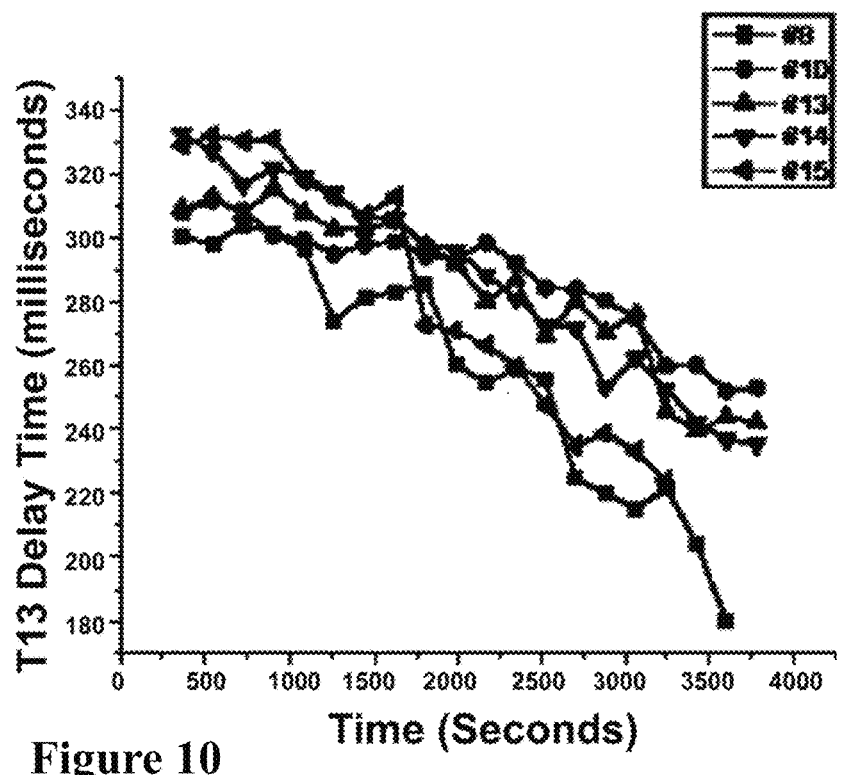
FIG. 10 is a graph illustrating fifteen-second averages of T1-3 values obtained within a minute of the cuff measurement.

Every one of the fifteen subjects studied exhibited statistically significant decreases in T1-3 as a function of LBNP. FIG. 10 displays fifteen-second averages of T1-3 for five other subjects not presented so far within a minute of the time the blood pressure cuff took its measurement. Given the results presented so far it is clear that a comparable presentation of cuff-derived pulse pressures would be meaningless.

Figure 11:
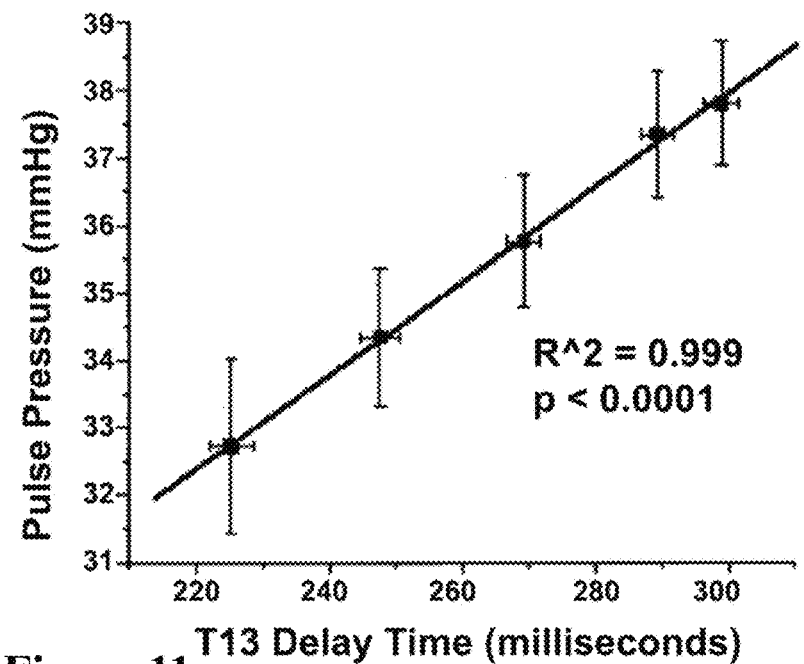
FIG. 11 is a graph illustrating the correlation between T1-3 PDA parameter and pulse pressure.

This study also presents a validation of the T1-3 parameter as being the arterial pulse parameter that correlates with pulse pressure. FIG. 11 presents a linear correlation of the T1-3 parameter and the cuff-derived pulse pressure, both of which appear to have a non-linear dependence on central blood loss based on the results presented in FIG. 8.

If they are indeed equivalent, their correlation should be linear, which it is at a high level of significance. In addition the correlation provides a statistically relevant conversion factor for relating T1-3 values to pulse pressures for individuals with T1-3 values in the neighborhood of 300 milliseconds at resting blood pressures.

FIGS. 10A and 10B show graphs illustrating results of tests using the disclosed system. FIG. 10A illustrates a comparison of the pulse line shapes obtained with a central line catheter with simultaneously obtained derivative pulse line shapes using the disclosed system. Of particular interest is the size of the renal reflection. The relative amplitudes of systolic peak and renal reflection obtained centrally match those obtained peripherally. Also illustrated in this Figure is a graph showing that in more than half the patients in the study there were periodic significant variations in systolic blood pressure as measured using the disclosed system. The disclosed data extends for four minutes and shows a series of drops, some lasting more than half a minute and extending over 20 or so heartbeats. The catheter observation time window missed the majority of these decreases because the protocol entry allowed 18 seconds of quiet observation at the renal artery region.

CONCLUSIONS

The results presented support that pulse pressure is a reliable indicator of central hypovolemia, decreasing early and with progressing decreasing magnitude as central blood loss increases in a non-linear manner. Equally important is the result that utilization of the technology of the present invention with use of the PDA algorithm provides a means to monitor pulse pressure, and therefore the progression of hemorrhage, reliably in a real-time fashion, an achievement that automatic cuff technologies are not likely to match. In light of the fact that, in order to be outcome-relevant, early detection of central hemorrhage by field equipped first responders is essential. The present invention's high portability and low battery power consumption enables a system that meets these requirements.

The results of this study also support the hypothesis that pulse pressure and the T1-3 parameter of the PDA algorithm are equivalent. The difference in the arrival times of the primary arterial pulse that is the left ventricular ejection and the iliac reflection pulse is determined by the differential velocities with which both pulses propagated along their arterial paths. In the case of the iliac reflection the path length is longer than that of the primary pulse by almost twice the length of the torso. More importantly, the pulse's arterial propagation velocities are pressure dependent, a relationship long known through the Moens-Korteweg equation, as noted in publication 5. One central insight is that both pulses travel at different velocities because their pressure amplitudes are different, the iliac reflection pulse amplitude, which is determined by the reflection coefficient of the iliac reflection site, being on the order of 40% of pulse pressure. Both pulses therefore load the arterial wall differently during their arterial travel, as a result of which their propagation velocities are different. The second insight is that, because the pressure/velocity response curve is non-linear—a result known since the 1960s based on Anliker's work, (publication 6)—both pulses accelerate and decelerate at different rates as the pressure rises and falls. The primary pulse experiences the highest changes in velocity as a function of changes in blood pressure because it is subject to the steepest section of the pressure/velocity response curve, while the iliac pulse, "running" at much lower pressure, changes velocity much more gradually. Changes in the time of arrival therefore then reflect changes in the differential arterial pressure that the two pulses experience. While this differential pressure is not exactly pulse pressure—pulse pressure being the difference between the full pulse arterial pulse height and the diastolic pressure floor—it represents about 60% of it, assuming the previously stated iliac reflection coefficient. More importantly, as the results of this study indicate, it tracks the changes in pulse pressure at a very high time resolution.

This time resolution is a significant benefit of measuring T1-3 over pulse pressure because it offers higher resolution. The results indicate the equivalence of a change of about 200 milliseconds in T1-3 to a variation of about 8 mmHg in pulse pressure over the entire range of a simulated central blood loss in excess of 1 liter for this cohort of fit and relatively young subjects. Given the uncertainties in determining pulse pressures with automated cuffs, the likelihood of resolving variations on the order of a single mmHg as central blood loss commences is remote at best. In comparison, the possibility of resolving changes in T1-3 on the order of 10-20 milliseconds as central blood loss progresses is quite feasible based on the results presented.

One could argue that the pulse pressure changes to be expected might be larger, given the results of the Convertino study (2), which recorded average changes in' pulse pressure of 18 mmHg. While this change in pulse pressure would likely still be difficult to resolve reliably with standard BP equipment the difference in the studies' results may point out another issue. As stated above, one reason for the difference in pulse pressure variations may be the difference in age and fitness of the respective participants. The average age of the subjects in the Convertino study was 42 years, as compared to 24.3 years in this study. Likewise, the average resting systolic blood pressure was 129 mmHg in the Convertino study as compared to 105 mmHg in this study, while the average pulse pressure was 51 mmHg compared to 37 mmHg. It is well known that pulse pressure rises as arterial walls harden, such as due to normal aging or pathological influences. Similar differences in subject groups differentiated by age or vascular health, such as diabetic patients, have been observed in the T1-3 parameter.

Young athletes typically have T1-3 delay times in the range of 300 milliseconds while vascularly challenged subjects have T1-3 delay times in the low 200 millisecond range, at comparable blood pressures and heart rates. The obvious explanation is that delay times between the two pulses shorten as pulse propagation velocities increase with hardening arterial walls. Since the subject group studied here is arguably more representative of today's armed forces membership, one of the primary target populations for early hemorrhagic shock detection, the results of this study further buttress the relevance of utilizing T1-3 as an early indicator in a combat environment because it is this group that likely will have the lowest resting pulse pressures and, correspondingly, largest T1-3 values.

FIGS. 9 and 10 show graphs illustrating results of tests using the disclosed system.

BROAD SCOPE OF THE INVENTION

All documents, patents, journal articles, and other materials cited in the present application are hereby incorporated by reference.

Although the present invention has been fully described in conjunction with several embodiments thereof with reference to the accompanying drawings, it is to be understood that various changes and modifications may be apparent to those skilled in the art, Such changes and modifications are to be understood as included within the scope of the present invention as defined by the appended claims, unless they depart therefrom.

While illustrative embodiments of the invention have been described herein, the present invention is not limited to the various preferred embodiments described herein, but includes any and all embodiments having equivalent elements, modifications, omissions, combinations (e.g., of aspects across various embodiments), adaptations and/or alterations as would be appreciated by those in the art based on the present disclosure. The limitations in the claims are to be interpreted broadly based on the language employed in the claims and not limited to examples described in the present specification or during the prosecution of the application, which examples are to be construed as non-exclusive. For example, in the present disclosure, the term "preferably" is non-exclusive and means "preferably, but not limited to." In this disclosure and during the prosecution of this application, means-plus-function or step plus-function limitations will only be employed where for a specific claim limitation all of the following conditions are present in that limitation: a) "means for" or "step for" is expressly recited; b) a corresponding function is expressly recited; and c) structure, material or acts that support that structure are not recited, in this disclosure and during the prosecution of this application, the terminology "present invention" or "invention" may be used as a reference to one or more aspect within the present disclosure. The language present invention or invention should not be improperly interpreted as an identification of criticality, should not be improperly interpreted as applying across all aspects or embodiments (i.e., it should be understood that the present invention has a number of aspects and embodiments) and should not be improperly interpreted as limiting the scope of the application or claims. In this disclosure and during the prosecution of this application, the terminology "embodiment" can be used to describe any aspect, feature, process or step, any combination thereof, and/or any portion thereof, etc. In some examples, various embodiments may include overlapping features. In this disclosure, the following abbreviated terminology may be employed: "e.g." which means "for example".

What is claimed is:

1. A method of early detection of total blood volume changes in an animate being by time based, real time monitoring of arterial pressure pulse waveforms as an immediate indicator of blood volume change comprising the steps of:
positioning a noninvasive sensor at a single arterial pulse detection site of said animate being;
recording, with said sensor, arterial pressure pulse waveforms generated by said animate being;
gathering, in real time, with a microprocessor, arterial pressure pulse waveform data from said sensor;
storing said arterial pressure pulse waveform data on a non-transitory computer readable medium as said data is received from said sensor;
running a pulse decomposition analysis algorithm, with said microprocessor, as said data is received from said sensor, said pulse decomposition algorithm capable of monitoring arrival time differences of pulses within said arterial pressure pulse waveform, in order to:
a) locate within each of said arterial pressure pulse waveforms a primary constituent systolic pulse, renal constituent reflection pulse, and iliac reflection constituent pulse,
b) extract from each of said primary constituent systolic pulse, and said iliac reflection constituent pulse a primary constituent systolic peak, and iliac reflection constituent peak, respectively, and
c) identify in real time a millisecond time of arrival of said primary systolic constituent peak and said iliac reflection constituent peak within each of said arterial pressure pulse waveforms recorded;
calculating in real time, with said microprocessor, a millisecond time difference between said arrival time of said primary systolic constituent peak and said arrival time of said constituent iliac reflection peak,
generating, with said microprocessor, real time arterial pressure pulse time difference data based on said time difference between arrival time of said primary systolic constituent peak and arrival time of said constituent iliac reflection peak;
storing on a non-transitory computer readable medium said arterial pulse time difference data,
comparing in real time, with said microprocessor, said arterial pressure pulse time difference data generated with previously stored arterial pressure pulse time difference data to monitor change in said arterial pulse time difference data;
monitoring, with said microprocessor, said arterial pressure pulse time difference of each and arterial pressure pulse recording in real time over a predetermined period of time, and
displaying said time difference data for observation;
wherein said arterial pressure pulse time difference data indicates a real-time time difference between said arrival time of said primary systolic constituent peak and said arrival time of said constituent iliac reflection peak of each of said arterial pressure pulse waveforms read, and wherein said arterial pressure pulse time difference directly corresponds to changes in blood volume in said animate being that predict in real time the onset of hypovolemia or hypervolemia.

2. The method of claim 1, wherein multiple arterial pressure pulse time difference data readings are produced within the predetermined period of time in order to allow comparisons between the multiple arterial pressure pulse time difference data readings.

3. The method of claim 2, further comprising the step of determining blood volume trends for a person by monitoring said multiple arterial pressure pulse time difference data readings constantly for a predetermined period of time of at least several hours.

4. The method of claim 2, wherein the microprocessor uses the arterial pulse time difference data gathered during said predetermined period of time to establish an arterial pulse parameter baseline value for said animate being from which to determine deviations from said baseline.

5. The method of claim 1, where said predetermined period of time is at least about fifteen seconds.

6. The method of claim 1, wherein said predetermined period of time is constant and during said period of time said animate being is undergoing a surgical procedure.

7. The method of claim 1, wherein said predetermined period of time is followed by multiple subsequent predetermined periods of time, each of said subsequent predetermined periods time being discontinuous from a prior predetermined period of time and a successive period of time over a period of at least a half hour.

8. The method of claim 1, further comprising the step of indicating changing trends in blood volume by monitoring and storing constantly said arterial pressure pulse time difference data for a predetermined period of time to indicate in real time the presence of decreasing time differences in said arterial pulse time difference data predictive of progressive hypovolemia or increasing arterial pulse time difference data predictive of hypervolemia.

9. The method of claim 1, wherein said previously stored arterial pressure pulse time difference data comprises arterial pressure pulse time difference data for said animate being, and/or a comparable animate being group.

10. The method of claim 1, wherein storing the data further comprises the step of determining, using said microprocessor, said changes in blood volume based on said time difference data gathered during said predetermined period of time.

11. A computerized method of early detection of blood volume changes by time based, real time monitoring of arterial pressure pulse waveforms for indication of hypovolemia or hypervolemia in an animate being, comprising the steps of:
positioning a noninvasive sensor at a single arterial pulse detection site;
reading with said sensor, arterial pressure pulse waveforms generated by said animate being;
gathering, in real time, with a microprocessor, arterial pressure pulse waveform data from said sensor;
storing said arterial pressure pulse waveform data on a non-transitory computer readable medium as said data is received from said sensor;
locating within said arterial pulse pressure waveform data a primary constituent systolic pulse, renal constituent reflection pulse, and an iliac reflection constituent pulse,
identifying in real time a millisecond arrival time of said primary systolic constituent peak and said constituent iliac reflection peak,
calculating in real time, with said microprocessor, a time difference in milliseconds between said arrival time of said primary systolic constituent peak and said arrival time of said constituent iliac reflection peak,
determining an arterial pulse parameter based on said time difference between arrival of said primary systolic constituent peak and arrival of said constituent iliac reflection peak, to create arterial pulse parameter data, storing said arterial pulse parameter data, and comparing each of said arterial pulse parameter data with previously stored arterial pulse parameter data for an increase or decrease, wherein calculating, with a microprocessor, a change in said arterial pulse parameter data compared to prior, stored, arterial pulse parameter data indicates a real-time change in blood volume with an increase between said arterial pulse parameter data over time indicating hypervolemia and a decrease between said arterial pulse parameter data over time indicating hypovolemia, each of said arterial pulse parameter data being stored in a computer.

12. The method of claim 11, wherein said previously stored arterial pressure pulse time difference data comprises arterial pressure pulse time difference data for said animate being, and/or a comparable group of animate beings.

13. The method of claim 12, wherein said previously stored arterial pressure pulse time difference data is stored on a non-transitory computer readable medium, and the method further comprises the steps of the computer generating output data, wherein said output data comprises time difference data for the time difference between said arterial pulse parameter data over a predetermined continuous period of time, said predetermined continuous period of time producing multiple time difference data readings for comparison, to predict in real time onset of progressive central hypovolemia or hypervolemia.

14. The method of claim 11, wherein the method further comprises the step of determining, using the microprocessor, trends and/or base lines for said animate being by monitoring for a plurality of intermittent testing intervals for extended periods of time.

* * * * *